(12) United States Patent
Lutz et al.

(10) Patent No.: US 7,544,366 B1
(45) Date of Patent: *Jun. 9, 2009

(54) METHOD AND SKIN CLEANSING COMPOSITIONS FOR DERMATOLOGICAL BASIC TREATMENT

(75) Inventors: Christian Lutz, Dornach (CH); Peter Huber, Binningen (CH)

(73) Assignee: Permamed AG, Therwil (CH)

( * ) Notice: Subject to any disclaimer, the term of this patent is extended or adjusted under 35 U.S.C. 154(b) by 891 days.

This patent is subject to a terminal disclaimer.

(21) Appl. No.: 10/747,382

(22) Filed: Dec. 29, 2003

Related U.S. Application Data

(63) Continuation-in-part of application No. 10/308,693, filed on Dec. 3, 2002, now Pat. No. 6,805,874.

(51) Int. Cl.
*A61K 8/02* (2006.01)
(52) U.S. Cl. .................................................. 424/401
(58) Field of Classification Search ................. 424/101
See application file for complete search history.

(56) References Cited

U.S. PATENT DOCUMENTS

| | | | | |
|---|---|---|---|---|
| 4,883,659 A | * | 11/1989 | Goodman et al. | 424/78.03 |
| 4,976,953 A | * | 12/1990 | Orr et al. | 424/47 |
| 5,439,682 A | | 8/1995 | Wivell et al. | 724/401 |
| 5,653,970 A | * | 8/1997 | Vermeer | 424/70.24 |
| 5,691,287 A | * | 11/1997 | Villars et al. | 510/151 |
| 5,883,059 A | | 3/1999 | Furman et al. | 510/130 |
| 6,099,849 A | | 8/2000 | Mansouri | 424/401 |
| 6,805,874 B1 | * | 10/2004 | Lutz et al. | 424/401 |
| 2003/0190371 A1 | * | 10/2003 | Graaf et al. | 424/642 |

OTHER PUBLICATIONS

Package inserts: "Dermel® Dermokosmetische Waschemulsion bei trockener Haut mit Rückfettungskomplex".
Package inserts: "Dermel® Dermokosmetische Waschemulsion hautberuhigend mit 5% Polidocanol".
Package inserts: "Dermel® Dermokosmetiche Waschemulsion bei sensibler Haut mit Protectiv-Komplex".

* cited by examiner

*Primary Examiner*—Johann R Richter
*Assistant Examiner*—Danielle Sullivan
(74) *Attorney, Agent, or Firm*—Gifford, Krass, Sprinkle, Anderson & Citkowski, P.C.

(57) ABSTRACT

The invention provides methods of dermatological basic treatment including the steps of pre-treating the skin with a composition that comprises a mild anti-microbial agent, a buffer that adjusts the skin pH to slightly acidic and an agent that forms a protective layer on the skin. This basic treatment has the effect of extraordinarily mild cleansing and sanitizing, restoring lipids, and providing a protective coating to the skin. Basic treatment may be followed by appropriate dermatological therapy. The invention further provides suitable compositions to be used in the dermatological basic treatment.

28 Claims, No Drawings

METHOD AND SKIN CLEANSING COMPOSITIONS FOR DERMATOLOGICAL BASIC TREATMENT

RELATED APPLICATION

This application is a continuation-in-part of U.S. patent application Ser. No. 10/308,693 filed Dec. 3, 2002 now U.S. Pat. No. 6,805,874.

BACKGROUND OF THE INVENTION

All dermatological treatment should begin with skin cleansing. However, the wrong type of skin cleansing can jeopardize the success of a dermatological treatment. In particular, use of a method of cleansing which is too vigorous, which exposes the skin to extremes of pH, or which delipidates the skin can cause damage to skin in need of therapy. In addition, improper cleansing may actually decrease the effectiveness of a dermatological therapy by impeding uptake of a pharmacological agent due to unbalanced pH or overly dry skin surface conditions. Thus, there is a continuing need for a method of basic treatment which cleanses and sanitizes the skin prior to dermatological treatment, enhances dermatological treatment and inhibits relapse between treatments, and there is a continuing need for compositions suitable for such a basic treatment which cleanses and sanitizes the skin and prevents relapses.

Mild skin care products for skin cleansing are known in the art. In U.S. Pat. No. 6,099,849, a skin care product moisturizing the skin is disclosed. This product contains hydroxyapatite to enhance absorption, and an anti-microbial in order to reduce the risk of infection by pathogens. Although it is claimed that treatment with this composition shields the skin from loss of moisture and from exposure to chemicals and detergents, the protection provided by this known composition is not optimal. Further mild skin cleansing containing a mixture of surfactants, moisturizing components and anti-bacterials are disclosed in U.S. Pat. No. 5,883,059. The skin cleansing compositions disclosed in U.S. Pat. No. 5,439,682 are also based on a mixture of different mild surfactants and moisturizing components.

SUMMARY OF THE INVENTION

Proper cleansing of skin is particularly important in relation to dermatological treatment but difficult to achieve. The skin must be sanitized in order to effectively protect the skin, yet standard cleansing techniques used for healthy skin may irritate and exacerbate dermatological disorders. The cleansing methods described herein overcome these long-standing problems, and, when used with the compositions detailed hereunder provide an efficient dermatological basic treatment of affected skin.

Methods of dermatological basic treatment as detailed herein generally include the steps of treating the skin with a composition that comprises a mild anti-microbial agent, a buffer that adjusts the skin pH to slightly acidic and an agent that forms a protective layer on the skin. This basic treatment has the effect of extraordinarily mild cleansing and sanitizing, restoring lipids, and providing a protective coating to the skin. Basic treatment may be followed by appropriate dermatological therapy.

The skin cleansing and basic treatment method according to the present invention has a number of aspects that contribute to the beneficial effect. For example skin cleansing according to the inventive method is extraordinarily mild, and compositions provided for cleansing are hypoallergenic. Compositions provided for basic treatment are particularly effective since they include an anti-microbial agent as a basic therapeutic agent. The basic treatment step further contributes to restoring and/or maintaining an appropriate therapeutic slightly acid skin pH. A composition provided for the basic treatment has the particular property of shielding the skin from environmental insults by leaving a protective film. The protective film contributes to restoring lipids to the skin and regenerating a lipid layer of the skin. This protective layer further contributes to maintaining an anti-microbial effect on the skin and may optionally contain soothing agents.

DETAILED DESCRIPTION OF THE INVENTION

The term "skin" as used herein is intended to mean the epidermis and this includes the scalp, external vagina area, anus, and skin regions having pathological conditions such as irritation, infection and disease, such as mycosis, acne, eczema, or the like.

The term "cleansing composition" is intended to mean a composition as a washing emulsion, used on any region of the body.

The first step in each dermatological treatment is always an optimal and mild cleansing of the sensitive and affected skin and therefore is the basis and starting point of each therapeutic treatment of skin diseases or prevention of relapses of skin diseases. Besides the cleansing, the basic treatment according to this invention, with its anti-microbial, i.e. anti-bacterial and anti-mycotic, and its skin protective and lipo-regenerating effect, helps to maintain the physiological acid milieu of the skin in skin affections such as dermatomycosis, pruritus senilis, eczema or acne. Additionally to the cleansing, the basic treatment provides a prophylactic effect as the compositions of this invention help to prevent from relapses in dermatomycosis and other skin diseases such as eczema.

A method of a dermatological basic treatment according to the present invention includes the steps of:

(a) providing an extraordinarily mild and hypoallergenic skin cleansing composition comprising an anti-microbial agent, a buffer which adjusts skin pH to a range of approximately 4.0-6.0, and an agent which forms a protective lipo-regenerating layer on the skin;

(b) applying the composition to the wet skin as a washing emulsion, whereby the composition cleanses and sanitizes the skin;

(c) rinsing the skin with water, whereby the composition forms a protective lipo-regenerating film on the skin; and optionally (d) subjecting the skin to a specific dermatological treatment.

An additional embodiment of a method of a dermatological basic treatment according to the present invention includes the steps of:

(a) providing an extraordinarily mild and hypoallergenic skin cleansing composition comprising an anti-microbial agent, an anti-itching agent, a buffer which adjusts skin pH to a range of approximately 4.0-6.0, and an agent which forms a protective lipo-regenerating layer on the skin;

(b) applying the composition to the wet skin as a washing emulsion, whereby the composition cleanses and sanitizes the skin;

(c) rinsing the skin with water, whereby the composition forms an anti-itching and protective, lipo-regenerating film on the skin; and optionally (d) subjecting the skin to a specific dermatological treatment.

At the beginning of each dermatological treatment stands the extraordinarily mild cleansing of normal, sensitive or affected skin. Particularly in affected skin, the wrong type of skin cleansing can jeopardize the success of the dermatological treatment. Therefore, the compositions of the invention comprise cleansing substances which are particularly mild to the skin. The compositions of the invention comprise a buffer maintaining the pH value of the skin at its physiological level, e.g. between pH 4.0 and 6.0, preferably between pH 5.0 and 5.8. Furthermore the compositions of the invention are hypoallergenic. They do not contain additional preservatives and are free from allergenic coloring agents and perfumes.

The basic treatment according to the invention cleanses and sanitizes the skin when the composition is applied onto the skin. Cleansing is best performed when the skin is wet, i.e. when the skin is humid, to allow proper distribution and interaction of the cleansing composition with the skin. On rinsing the skin, the cleansing composition is diluted on the skin, and thereby a film is formed on the skin which has protective lipo-regenerating properties and provides anti-microbial, i.e. anti-bacterial and anti-mycotic effects, and, depending on the particular ingredients of the composition, also a skin-soothing and/or anti-pruritic, i.e. anti-itching effect. The protective film built on the skin on rinsing with water remains on the skin for an extended period of time.

The lipo-regenerating film formed during the inventive method is essential for the success of the basic treatment, and the composition to be applied in the method is chosen such as to provide the desired results.

The lipo-regenerating film on the skin forms a protective layer preventing pathological bacteria and fungi from installing themselves on the skin, and therefore the treatment according to the invention may act also as a prophylaxis against relapses. In case of dry skin diseases, the lipo-regenerating film prevents relapse to dry skin conditions and pruritus. The hypoallergenic features of the compositions according to the invention prevent irritations and allergies.

The combination of the extraordinarily mild skin cleansing and the formation of a lipo-regenerating film is optimally preparing the affected skin for a specific dermatological treatment. The different skin parameters of the affected skin are influenced in such a way that the specific dermatological treatment applied works with an improved efficacy. The result will be a considerable reduction in the duration of the treatment time and a more efficient prevention of relapses of skin diseases when compared with a dermatological treatment omitting the cleansing and formation of a lipo-regenerating film.

A cleansing composition provided for use in a method of the present invention is hypoallergenic and acts to cleanse, sanitize, restore lipids and form a protective, lipo-regenerating film on the skin. A cleansing composition typically comprises a balanced mixture of suitable lipo-regenerating/protective film forming agents, a mild anti-microbial agent, a buffer system and a very mild surfactant as a cleansing agent, and may further include supplementary components. The mixture of film forming agents consists of at least one lipid type and one polyquat type component, preferably two ore more, e.g. two, three or four, lipoid type components and one or more, e.g. one or two, polyquat type components, in particular three compatible components such as two lipoid type components and one polyquat type component with complementary properties. It is essential that the components are chosen in a balanced way which guarantees the formation of a lipo-regenerating and protective film on application of the cleansing method of the invention. A particularly beneficial effect of these ingredients is observed when preferred compositions are used in the method of the invention. Specific formulations of skin cleansing emulsions are given hereinbelow.

Without wishing to be bound by theoretical considerations, the lipo-regenerating system of the invention includes one or more lipoid type components that are insoluble or only slightly soluble in water. These lipoid type components are solubilized in the cleansing composition, and are deposited on the skin together with the polyquat type component or components when the skin is rinsed with water after the skin cleansing with the provided composition. The deposited lipoids and polyquats form a lipo-regenerating non-occlusive protective film that may be drawn onto the skin, and act to restore lipids to the skin and/or encourage lipid regeneration within the skin.

Generally, lipoid type components of the lipo-regenerating agent mixtures are triglycerides (fats), fatty acids, fatty alcohols and derivatives thereof, wherein the fatty acid and fatty alcohol is saturated or unsaturated and straight or branched chain. Derivatives of fatty acids are e.g. esters, amides and salts. Derivatives of fatty alcohols are e.g. ethers and esters. Preferred lipoid type components include glycerylated fatty acids, ethoxylated fatty acids and ethoxylated fatty alcohols, propoxylated fatty acids and propoxylated fatty alcohols, and mixtures thereof, wherein the average number of moles of ethylene oxide or propylene oxide varies from 1 to 50 and the chain length of the fatty acids or fatty alcohols varies from 6 to 22, and the fatty acid is saturated or unsaturated, and straight chain or branched chain. Particularly preferred are ethoxylated fatty acids wherein the average number of ethylene oxide varies from 1 to 50, and the chain length of the fatty acid varies from 6 to 22, in particular coceth-6. Also particularly preferred are glycerylated fatty acids wherein the chain length of the fatty acid varies from 6 to 22, is saturated or unsaturated, and straight chain or branched chain, in particular glyceryl oleate.

Polyquat type components of the lipo-regenerating agents include polyquaternium-1 up to polyquaternium-50, preferably polyquaternium-2, guar hydroxypropyltrimonium chloride, or hydroxypropyl guar hydroxypropyltrimonium chloride, related quaternized ammonium compounds, and mixtures of the mentioned polyquat type components.

The preferred mixture of lipo-regenerating agents comprises two lipoid type components, such as an ethoxylated fatty acid, in particular coceth-6, and a glycerylated fatty acid, in particular glyceryl oleate, and one polyquat type component, such as polyquaternium-2.

An anti-microbial agent is directly beneficial in inhibiting micro-organisms such as bacteria, fungi, yeast and viruses involved in dermatological pathology as well as inhibiting microbes which may infect the skin secondary to the primary condition. For example, an anti-microbial agent inhibits *Staphylococcus aureus, Candida parapsilosis, Candida albicans, Pseudomonas aeruginosa, Apergillus niger, Enterococci, Pityrosporum ovale, Microsporum gypseum, Gardnerella vaginalis, Trichophyton mentagrophytes* and *Propionibacterium acnes*. Where it is desirable to inhibit a specific organism, a suitable anti-microbial agent may be tested for inhibitory properties when included in a composition by a test known to one skilled in the art, such as an agar diffusion test.

Examples of anti-microbial agents that could be used in compositions of the invention, in particular anti-bacterial or anti-mycotic agents, are benzalkonium chloride, benzoic acid, benzoxonium chloride, benzyl alcohol, 2-bromo-2-nitropropane-1,3-diol, 5-bromo-5-nitro-1,3-dioxane, bromochlorophene, camphor benzalkonium methosulfate, captan, cetrimonium bromide, cetrimonium chloride, cetylpyridinium chloride, climbazol, chloracetamide, chlorhexidine and its salts, p-chloro-m-cresol, chlorphenesin, chloroxylenol, chlorophen, chlorobutanol, o-cymen-5-ol, dehydroacetic acid, dibromodicyanobutan, dibromohexamidin, dibromopropamidin, dichlorobenzyl alcohol, dichlorophenyl imidazoldioxolan, dimethyloxazolidin, DMDM hydantoin, dodecylguanidine acetate, hexamidine diisothionate, hexachlorophen, hexetidin, iodopropynyl butylcarbamate, lauryl isoquinolinium bromide, methyldibromo glutaronitrile, methylolchloracetamide, phenethyl alcohol, phenoxyethanol, phenoxypropanol, o-phenylphenol, piroctone olamine, polyaminopropyl biguanide, potassium sorbate, potassium undecylenoyl hydrolyzed collagen, quaternium-15, salicylic acid, sodium benzoate, sodium dehydroacetate, sodium hydroxymethylglycinate, sodium o-phenylphenate, sorbic acid, triclocarban, triclosan, undecylenic acid and its derivatives, zinc cysteate, zinc gluconate, zinc pyrithione, or zinc sulfate.

Derivatives of undecylenic acid useful as anti-microbial agents are e.g. esters, such as methyl ester, isopropyl ester, glyceryl ester, ethoxylated soya sterol ester, or ethoxylated PHB ester, or amides, such as monoethanolamide, monoethanolamide derivatives such as monoethanolamide (MEA) sulfosuccinate salts, diethanolamide, protein condensates, e.g. potassium undecylenoyl hydrolyzed animal collagen, and quaternized 3-aminopropyl-amide, e.g. undecylenamidopropyltrimonium methosulfate.

Particularly preferred as an anti-microbial in a composition according to the invention is disodium undecylenamido MEA-sulfosuccinate, which is well tolerated in skin and mucous.

A buffer system in a cleansing composition acts to maintain the pH of the composition at a slightly acidic pH, between pH 4.0 and pH 7.0. More preferably, the buffer maintains the pH of the composition between pH 4.5 and pH 6.0. For example, suitable buffers are lactate buffer, such as lactic acid and sodium, potassium or ammonium lactate, citrate buffer, such as citric acid and sodium, potassium or ammonium citrate, phosphate buffer, such as sodium dihydrogen phosphate and disodium hydrogen phosphate or corresponding potassium or ammonium salts, or acetate buffer, such as acetic acid and sodium, potassium or ammonium acetate. A buffer can also be formed using the corresponding buffer acid and sodium or potassium hydroxide or ammonia, or also using a buffer salt and a mineral acid, e.g. hydrochloric, sulfuric acid, or an organic sulfonic acid. A preferred buffer system consists of a citrate buffer, in particular formed from citric acid and sodium citrate. Another preferred buffer system consists of a lactate buffer, in particular formed from lactic acid and sodium lactate.

A cleansing agent is included in compositions for cleansing skin that acts to remove dirt in general and may also remove built up skin secretions, cosmetics and remnants of previous applications of dermatological treatments. A cleansing agent may include any such agent recognized in the art that is extraordinarily mild, hypoallergenic, safe and effective for cleansing skin. In particular, a cleansing agent may include a surfactant, such as an anionic, nonionic, amphoteric, zwitterionic and/or cationic surfactant. Examples of suitable surfactants are castor oil based amidobetaine, e.g. ricinoleamidopropyl betaine, disodium cocamphodiacetate, cocamidopropyl betaine, sodium cocoamphoproprionate, cocamidopropyl hydroxysultaine, sodium cocoyl isethionate, potassium cocoyl hydrolyzed collagen, disodium lauroamphodiacetate, alkyl glucosides, e.g. decyl glucoside, various fatty alcohol sulfates, e.g. lauryl sulfate, or ethoxylated fatty alcohol sulfates, e.g. laureth sulfate, as their sodium, magnesium, ammonium or potassium salts, and various fatty alcohol sulfosuccinates, e.g. disodium lauryl sulfosuccinate, disodium cocamido MEA-sulfosuccinate, disodium lauramido MEA-sulfosuccinate or disodium ricinoleamido MEA-sulfosuccinate, and ethoxylated fatty alcohol sulfosuccinates, e.g. disodium PEG-5 laurylcitrate sulfosuccinate, disodium laneth-5 sulfosuccinate, disodium laureth sulfosuccinate, disodium PEG-4 cocamido MIPA sulfosuccinate, or disodium sitostereth-14 sulfosuccinate, corresponding magnesium or potassium salts, and general equivalents thereof recognized in the art.

Preferred mild surfactants are e.g. disodium cocoamphodiacetate, cocamidopropyl hydroxysultaine, disodium laureth sulfosuccinate and decyl glucoside. A further particularly preferred mild surfactant is disodium undecylenamido MEA-sulfosuccinate which has also anti-microbial properties, as described hereinabove.

Supplementary components in a provided cleansing composition may include e.g. a hydrating agent or moisturizer, e.g. glycerol, propylene or pentylene glycol, fructose, glucose, lactic acid and its sodium salt, lactose, mannitol, melibiose, PCA and sodium PCA, sorbitol, urea, and the like, a solubilizer, e.g. PEG-4 up to PEG-2000, preferably PEG-20, PEG-20 to PEG-60 hydrogenated castor oil, PEG-60 sorbitan stearate, poloxamer 184, 237 or 407, polysorbate 20 to 85, ricinoleth-40, steareth-25, and equivalents recognized in the art, a thickening agent, stabilizer or thixotropic agent, e.g. acrylate/alkyl acrylate copolymers, carbomer, carrageenan, cellulose gum, cocamide DEA, MEA or MIPA, stearamide MEA, cocamidopropylaminoxide, hydroxymethyl-, -ethyl- or -propylcellulose, methylcellulose or methyl hydroxyethylcellulose, PEG-55 propylene glycol oleate, PEG-120 methyl glucose dioleate, PEG-150 distearate or PEG-200 glyceryl tallowate, polyvinyl alcohol, xanthan gum or the like. Examples of some preferred additional components are glycerol, PEG-20 and PEG-120 methyl glucose dioleate.

A supplementary component according to the invention may be a basic remedial agent for the treatment of a dermatological condition distinct from and in addition to the treatment administered following cleansing with a cleansing emulsion. A basic remedial agent may be e.g. an anti-pruritic agent for relief from itching due to an underlying dermatological disorder. Examples of such anti-pruritic agents are local anesthetics, like e.g. articain, benzocain, bupivacain, butanilicain, butoxycain, cinchocain, fomocain, lidocain, mepivacain, oxetacain, oxybuprocain, pramocain, prilocaln, procain, proxymetacain, tolycain, or tetracain, or local anti-histaminics, like e.g. bamipin, chlorphenoxamin, clemastin, dimetinden, diphenhydramin, diphenylpyralin, isoprenalinsulfat, pheniramin, tolpropamin, or tripeleunamin, or other anti-pruriginosa, e.g. chlorobutanol, crotamiton, quinisocain, laureth-5, 6, 7, 8, 9, 10, 11, 12, or 13, or the like.

A preferred anti-itching agent is laureth-9, also referred to as polidocanol and polidocanol 600, i.e. a dodecyl ether of polyethylene glycol.

Cleansing compositions are provided in forms such as liquid, gel, foam, cream, solid block or equivalents known in the art to be compatible with topical application to the skin. Preferably the cleansing compositions are liquids on an aqueous basis.

Compositions considered in the invention are, for example, compositions comprising:

(a) disodium undecylenamido MEA-sulfosuccinate as a mild anti-microbial agent;

(b) a lipo-regenerating system consisting of two or more lipoid type components and one or more polyquat type components;

(c) a buffer between pH 4 and 7; and (d) a mild surfactant or surfactant mixture.

Preferred compositions of the invention comprise:

(a) disodium undecylenamido MEA-sulfosuccinate as a mild anti-microbial agent;

(b) a lipo-regenerating system consisting of coceth-6, glyceryl oleate and polyquaternium-2;

(c) a citric acid/sodium citrate or a lactic acid/sodium lactate buffer; and (d) a mild surfactant or surfactant mixture.

Particularly preferred compositions of the invention comprise:

(a) disodium undecylenamido MEA-sulfosuccinate as a mild anti-microbial agent;

(b) a lipo-regenerating system consisting of coceth-6, glyceryl oleate and polyquaternium-2;

(c) a citric acid/sodium citrate buffer; and (d) a surfactant mixture consisting of disodium cocoamphodiacetate, cocamidopropyl hydroxysultaine, disodium laureth sulfosuccinate, and decyl glucoside.

Other particularly preferred compositions of the invention comprise:

(a) disodium undecylenamido MEA-sulfosuccinate as a mild anti-microbial agent;

(b) a lipo-regenerating system consisting of coceth-6, glyceryl oleate and polyquaternium-2;

(c) a lactic acid/sodium lactate buffer; and (d) a surfactant mixture consisting of disodium cocoamphodiacetate, cocamidopropyl hydroxysultaine, disodium laureth sulfosuccinate, and decyl glucoside.

Disodium undecylenamido MEA-sulfosuccinate as a mild anti-microbial agent is preferably present in amounts of 0.1% to 10%, in particular 0.5% to 5%, especially 2 to 4%.

The preferred amounts of the components of the lipo-regenerating system are 0.1% to 15% coceth-6, in particular 1% to 10%, preferably 2% to 7% coceth-6; 0.1% to 10% glyceryl oleate, in particular 0.2% to 5%, preferably 0.3% to 2.5% glyceryl oleate; and 0.01% to 5% polyquaternium-2, in particular 0.1% to 2.5%, preferably 0.4% to 1.3% polyquaternium-2; such that the combined amount of the three lipo-regenerating agents amounts from about 0.2% to 30%, preferably from about 3% to 11% of the total composition. It is further preferred to add a solubilizer for the lipo-regenerating system, e.g. 0.1% to 15%, in particular 0.5% to 10%, preferably 1% to 6% PEG-20.

The citrate buffer is preferably made up of 0.1% to 5% citric acid and 0.1% to 5% sodium citrate, in particular 0.1% to 3% citric acid and 0.1% to 3% sodium citrate, preferably 0.2% to 2% sodium citrate and 0.2% to 2% sodium citrate such that the resulting pH is between 5 and 6.

The lactate buffer is preferably made up of 0.1% to 5% lactic acid and 0.1% to 5% sodium lactate, in particular 0.1% to 3% lactic acid and 0.1% to 3% sodium lactate, preferably 0.2% to 2% lactic acid and 0.3% to 3% sodium lactate such that the resulting pH is between 5 and 6.

The preferred amounts of the components of the surfactant mixture are 0.1% to 10% disodium cocoamphodiacetate, in particular 1% to 10%, preferably 4% to 8% disodium cocoamphodiacetate; 0.1% to 10% cocamidopropyl hydroxysultaine, in particular 1% to 10%, preferably 4% to 6% cocamidopropyl hydroxysultaine; 0.1% to 10% disodium laureth sulfosuccinate, in particular 0.5% to 5%, preferably 1% to 3% disodium laureth sulfosuccinate; and 0.1% to 15% decyl glucoside, in particular 1% to 10%, preferably 4% to 8% decyl glucoside. It is further preferred to add a hydrating agent, e.g. glycerol, preferably in an amount of 1% to 40%, in particular 5% to 35%, preferably 10% to 30%, and a thickening agent, e.g. PEG-120 methyl glucose dioleate, preferably in a amount of 0.1% to 10%, in particular 0.5% to 10%, preferably 1% to 5%.

A further preferred component of the composition is an anti-itching compound, e.g. laureth-9, preferably in amounts of 0.1% to 15%, in particular 1% to 10%, especially 4% to 6%.

Through a continuous application of provided compositions and the cumulative effect mentioned hereinbefore, the physiological milieu of the affected skin is considerably ameliorated. After the washing process a protective film stays on the skin with lipo-regenerating, anti-bacterial and anti-mycotic properties as well as anti-itching properties in the case of compositions further comprising anti-pruritic compounds. This lipo-regenerating film restores the necessary lipids on the skin which is favorable for re-establishing a natural, physiological milieu. As this film stays on the surface of the skin it has a protective action and acts as a prophylaxis against relapses of skin diseases and supports and improves additional specific treatment.

Application of a provided composition is a step included in an inventive method for enhancing effectiveness of a dermatological basic treatment. Application may be performed by a skin care professional such as a physician, nurse or medical technician prior to dermatological treatment. In addition, application may be performed by a patient at home or in a treatment facility as a continuation and adjunct to a primary dermatological treatment.

Following application of a composition of the invention, it may be maintained in contact with affected skin for a period of time, appropriate to enhance the basic treatment. The maintenance on the skin is e.g. from 0.1 to about 10 minutes. In general, an appropriate time will be determined according to the type and severity of the underlying dermatological problem.

Removal of a provided cleansing composition may be effected by various means according to the desired result. In general, removal of the composition includes dilution of the applied composition by rinsing the skin with water. Rinsing removes a portion of water soluble substances and effects the deposit of lipo-regenerating/protective film forming components onto the skin. The deposited lipoids type components and polyquat type components form a lipo-regenerating non-occlusive protective film. The protective film may further contribute to enhance the dermatological basic treatment by maintaining remedial agents.

This innovative method with the protective film-building process is suitable in various dermatological conditions like e.g. pruritus, e.g. pruritus senilis, pruritus sine material, pruritus vulvae, pruritus ani, atopic dermatitis, psoriasis, acne vulgaris, infections such as dermatomycoses, candida or bacterial infections, seborrheic dermatitis, acute, sub-acute and chronic eczema, toxic and allergic contact eczemas, lichen planus, ichthyosis, lichen sclerosus, dermatitis herpetiformis, dry skin, xerotic dermatoses, warts, dermatoses, and urticaria.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods of a basic treatment, procedures, specific treatments, compositions, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

EXAMPLES

Example 1

Preparation of a Product for Sensitive Skin 5.0 g glyceryl oleate, 40.0 g PEG-20, 212.5 g glycerol, and 25.0 g coceth-6 are weighed out in a 2 L cup and heated up to about 60° C. in a water bath until a melt is resulting. Then 50.0 g cocamidopropyl hydroxysultaine, 50.0 g disodium cocoamphodiacetate, 65.0 g decyl glucoside, and 20.0 g disodium laureth sulfosuccinate are added one after the other at room temperature, and everything is mixed until homogenous with a winged mixer. 4.34 g polyquaternium-2 are added and again mixed at room temperature.

14.0 g sodium citrate are dissolved in 200 mL water with the help of a magnetic mixer. 30.0 g disodium undecylenoyl MEA-sulfosuccinate are added and stirred until homogenous. This mixture is added slowly under stirring to the original mixture, and stirring continued for approx. 30 minutes. A solution of 7.5 g citric acid in 100 mL water is added, and the mixture stirred for approx. 5 minutes. Then 23.1 g PEG-120 methyl glucose dioleate are added and the mixture stirred for approx. 30 minutes.

The pH value is measured and, if necessary, adjusted to a value of pH 5.2-5.8 with citric acid. The viscosity is adjusted to 1300-1900 mPa with PEG-120 methyl glucose dioleate. Water is added to make up 1000.00 g, and the mixture stirred until homogenous.

A further product for sensitive skin is obtained according to the procedure mentioned, but using the following components in the following amounts: 4.5 g glyceryl oleate, 40.0 g PEG-20, 212.5 g glycerol, 25.0 g coceth-6, 52.5 g cocamidopropyl hydroxysultaine, 52.5 g disodium cocoamphodiacetate, 67.5 g decyl glucoside, 20.0 g disodium laureth sulfosuccinate, 4.34 g polyquaternium-2, 18.0 g sodium lactate replacing sodium citrate, 30.0 g disodium undecylenoyl MEA-sulfosuccinate, 12.6 g lactic acid replacing citric acid, 24.5 g PEG-120 methyl glucose dioleate.

The pH value is measured and, if necessary, adjusted to a value of pH 5.0-5.8 with lactic acid. The viscosity is adjusted to 1300-1900 mPa with PEG-120 methyl glucose dioleate. Water is added to make up 1000.00 g, and the mixture stirred until homogenous.

Example 2

Preparation of a Product for Dry Skin 12.5 g glyceryl oleate, 40.0 g PEG-20, 170.0 g glycerol, and 55.0 g coceth-6 are weighed out in a 2 L cup and heated up to about 60° C. in a water bath until a melt is resulting. Then 47.5 g cocamidopropyl hydroxysultaine, 47.5 g disodium cocoamphodiacetate, 50.0 g decyl glucoside, and 20.0 g disodium laureth sulfosuccinate are added one after the other at room temperature, and everything is mixed until homogenous with a winged mixer. 8.68 g polyquaternium-2 are added and again mixed at room temperature.

14.0 g sodium citrate are dissolved in 160 mL water with the help of a magnetic mixer. 30.0 g disodium undecylenoyl MEA-sulfosuccinate are added and stirred until homogenous. This mixture is added slowly under stirring to the original mixture, and stirring continued for approx. 30 minutes. A solution of 7.5 g citric acid in 100 mL water is added, and the mixture stirred for approx. 5 minutes. Then 15.8 g PEG-120 methyl glucose dioleate are added and the mixture stirred for approx. 30 minutes.

The pH value is measured and, if necessary, adjusted to a value of pH 5.2-5.8 with citric acid. The viscosity is adjusted to 1300-1900 mPa with PEG-120 methyl glucose dioleate. Water is added to make up 1000.00 g, and the mixture stirred until homogenous.

A further product for dry skin is obtained according to the procedure mentioned, but using the following components in the following amounts: 11.25 g glyceryl oleate, 40.0 g PEG-20, 170.0 g glycerol, 55.0 g coceth-6, 47.5 g cocamidopropyl hydroxysultaine, 47.5 g disodium cocoamphodiacetate, 50.0 g decyl glucoside, 20.0 g disodium laureth sulfosuccinate, 8.68 g polyquaternium-2, 18.0 g sodium lactate replacing sodium citrate, 30.0 g disodium undecylenoly MEA-sulfosuccinate, 10.8 g lactic acid replacing citric acid, 17.5 g PEG-120 methyl glucose dioleate.

The pH value is measured and, if necessary, adjusted to a value of pH 5.0-5.8 with lactic acid. The viscosity is adjusted to 1300-1900 mPa with PEG-120 methyl glucose dioleate. Water is added to make up 1000.00 g, and the mixture is stirred until homogenous.

Example 3

Preparation of a Skin Soothing Product 20.0 g glyceryl oleate, 40.0 g PEG-20, 127.5 g glycerol, 50.0 g laureth-9, and 50.0 g coceth-6 are weighed out in a 2 L cup and heated up to about 60° C. in a water bath until a melt is resulting. Then 47.5 g cocamidopropyl hydroxysultaine, 47.5 g disodium cocoamphodiacetate, 50.0 g decyl glucoside, and 20.0 g disodium laureth sulfosuccinate are added one after the other at room temperature, and everything is mixed until homogenous with a winged mixer. 6.82 g polyquaternium-2 are added and again mixed at room temperature.

14.0 g sodium citrate are dissolved in 100 mL water with the help of a magnetic mixer. 30.0 g disodium undecylenoyl MEA-sulfosuccinate are added and stirred until homogenous. This mixture is added slowly under stirring to the original mixture, and stirring continued for approx. 30 minutes. A solution of 7.0 g citric acid in 90 mL water is added, and the mixture stirred for approx. 5 minutes. Then 21.0 g PEG-120 methyl glucose dioleate are added and the mixture stirred for approx. 30 minutes.

The pH value is measured and, if necessary, adjusted to a value of pH 5.2-5.8 with citric acid. The viscosity is adjusted to 1300-1900 mPa with PEG-120 methyl glucose dioleate. Water is added to make up 1000.00 g, and the mixture stirred until homogenous.

A further skin soothing product is obtained according to the procedure mentioned, but using the following components in the following amounts: 18.0 g glyceryl oleate, 40.0 g PEG-20, 127.5 g glycerol, 50.0 g laureth-9, 50.0 g coceth-6, 47.5 g cocamidopropyl hydroxysultaine, 47.5 g disodium cocoamphodiacetate, 50.0 g decyl glucoside, 20.0 g disodium laureth sulfosuccinate, 6.82 g polyquaternium-2, 18.0 g sodium lactate replacing sodium citrate, 30.0 g disodium undecylenoyl MEA-sulfosuccinate, 11.6 g lactic acid replacing citric acid, 24.5 g PEG-120 methyl glucose dioleate.

The pH value is measured and, if necessary, adjusted to a value of pH 5.0-5.8 with lactic acid. The viscosity is adjusted to 1300-1900 mPa with PEG-120 methyl glucose dioleate. Water is added to make up 1000.00 g, and the mixture stirred until homogenous.

The invention claimed is:

1. A composition comprising:
   (a) disodium undecylenamido MEA-sulfosuccinate as a mild anti-microbial agent;
   (b) a lipo-regenerating system consisting of two or more lipoid components and one or more polyquat components;
   (c) a buffer between pH 4 and 6; and
   (d) a mild surfactant or surfactant mixture.

2. The composition according to claim 1 wherein the lipo-regenerating system consists of coceth-6, glyceryl oleate and polyquaternium-2.

3. The composition according to claim 2 wherein the mild surfactant mixture consists of disodium cocoamphodiacetate, cocamidopropyl hydroxysultaine, disodium laureth sulfosuccinate, and decyl glucoside.

4. The composition according to claim 3 wherein the buffer is citric acid/sodium citrate buffer.

5. The composition according to claim 3 wherein the buffer is lactic acid/sodium lactate buffer.

6. The composition according to claim 4 comprising:
   (a) 0.1% to 10% disodium unidecylenamido MEA-sulfosuccinate;
   (b) 0.1% to 15% coceth-6, 0.1% to 10% glyceryl oleate and 0.01% to 5% polyquaternium-2;
   (c) 0.1% to 5% citric acid and 0.1% to 5% sodium citrate;
   (d) 0.1% to 10% disodium cocoamphodiacetate, 0.1% to 10% cocamidopropyl hydroxysultaine, 0.1% to 10% disodium laureth sulfosuccinate, and 0.1% to 15% decyl glucoside.

7. The composition according to claim 5 comprising:
   (a) 0.1% to 10% disodium undecylenamido MEA-sulfosuccinate;
   (b) 0.1% to 15% coceth-6, 0.1% to 10% glyceryl oleate and 0.01% to 5% polyquaternium-2;
   (c) 0.1% to 5% lactic acid and 0.1% to 5% sodium lactate;
   (d) 0.1% to 10% disodium cocoamphodiacetate, 0.1% to 10% cocamidopropyl hydroxysultaine, 0.1% to 10% disodium laureth sulfosuccinate, and 0.1% to 15% decyl glucoside.

8. The composition according to claim 6 further containing 0.1% to 15% PEG-20.

9. The composition according to claim 7 further containing 0.1% to 15% PEG-20.

10. The composition according to claim 6 further containing 1% to 40% glycerol.

11. The composition according to claim 7 further containing 1% to 40% glycerol.

12. The composition according to claim 6 further containing 0.1% to 10% PEG-120 methyl glucose dioleate.

13. The composition according to claim 7 further containing 0.1% to 10% PEG-120 methyl glucose dioleate.

14. The composition according to claim 6 further containing 0.1% to 15% laureth-9.

15. The composition according to claim 7 further containing 0.1% to 15% laureth-9.

16. The composition according to claim 4 comprising:
   (a) 0.50 to 5% disodium undecylenamido MEA-sulfosuccinate;
   (b) 1% to 10% coceth-6, 0.2% to 5% glyceryl oleate and 0.1% to 2.5% polyquaternium-2;
   (c) 0.1% to 3% citric acid and 1% to 3% sodium citrate;
   (d) 1% to 10% disodium cocoamphodiacetate, 1% to 10% cocamidopropyl hydroxysultaine, 0.5% to 5% disodium laureth sulfosuccinate, and 1% to 10% decyl glucoside.

17. The composition according to claim 5 comprising:
   (a) 0.5% to 5% disodium undecylenamido MEA-sulfosuccinate;
   (b) 1% to 10% coceth-6, 0.2% to 5% glyceryl oleate and 0.1% to 2.5% polyquaternium-2;
   (c) 0.1% to 3% lactic acid and 0.1% to 3% sodium lactate;
   (d) 1% to 10% disodium cocoamphodiacetate, 1% to 10% cocamidopropyl hydroxysultaine, 0.5% to 5% disodium laureth sulfosuccinate, and 1% to 10% decyl glucoside.

18. The composition according to claim 4 comprising:
   (a) 2% to 4% disodium undecylenamido MEA-sulfosuccinate;
   (b) 2% to 7% coceth-6, 0.3% to 2.5% glyceryl oleate and 0.4% to 1.3% polyquaternium-2;
   (c) 0.2% to 2% citric acid and 0.2% to 2% sodium citrate;
   (d) 4% to 8% disodium cocoamphodiacetate, 4% to 6% cocamidopropyl hydroxysultaine, 1% to 3% disodium laureth sulfosuccinate, and 4% to 8% decyl glucoside.

19. The composition according to claim 5 comprising:
   (a) 2% to 4% disodium undecylenamido MEA-sulfosuccinate;
   (b) 2% to 7% coceth-6, 0.0% to 2.5% glyceryl oleate and 0.4% to 1.3% polyquaternium-2;
   (c) 0.2% to 2% lactic acid and 0.2% to 2% sodium lactate;
   (d) 4% to 8% disodium cocoamphodiacetate, 4% to 6% cocamidopropyl hydroxysultaine, 1% to 3% disodium laureth sulfosuccinate, and 4% to 8% decyl glucoside.

20. The composition according to claim 18 further containing 1% to 6% PEG-20.

21. The composition according to claim 19 further containing 1% to 6% of PEG-20.

22. The composition according to claim 18 further containing 10% to 30% glycerol.

23. The composition according to claim 19 further containing 10% to 30% glycerol.

24. The composition according to claim 18 further containing 1% to 5% PEG-120 methyl glucose dioleate.

25. The composition according to claim 19 further containing 1% to 5% PEG-120 methyl glucose dioleate.

26. The composition according to claim 18 further containing 4% to 6% laureth-9.

27. The composition according to claim 19 further containing 4% to 6% laureth-9.

28. The composition according to claim 3 in the form of an aqueous liquid.

* * * * *